(12) United States Patent
Walsworth et al.

(10) Patent No.: US 9,541,512 B2
(45) Date of Patent: Jan. 10, 2017

(54) MULTI-COLOR NANOSCALE IMAGING BASED ON NANOPARTICLE CATHODOLUMINESCENCE

(75) Inventors: Ronald Walsworth, Newton, MA (US); Jeff Lichtman, Cambridge, MA (US); Narayanan Kasthuri, Cambridge, MA (US); David Glenn, Cambridge, MA (US); Huiliang Zhang, Cambridge, MA (US); Richard Schalek, Wakefield, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 268 days.

(21) Appl. No.: 14/125,934

(22) PCT Filed: Jun. 13, 2012

(86) PCT No.: PCT/US2012/042332
§ 371 (c)(1),
(2), (4) Date: Mar. 18, 2014

(87) PCT Pub. No.: WO2012/174173
PCT Pub. Date: Dec. 20, 2012

(65) Prior Publication Data
US 2014/0194314 A1    Jul. 10, 2014

Related U.S. Application Data (60) Provisional application No. 61/496,482, filed on Jun. 13, 2011.

(51) Int. Cl.
*G01N 23/225* (2006.01)
*H01J 37/22* (2006.01)
(Continued)

(52) U.S. Cl.
CPC .... *G01N 23/2254* (2013.01); *G01N 33/54373* (2013.01); *H01J 37/22* (2013.01);
(Continued)

(58) Field of Classification Search
CPC ................. G01N 23/2254; G01N 33/54373; H01J 37/244; H01J 37/22
See application file for complete search history.

(56) References Cited

U.S. PATENT DOCUMENTS

2006/0269483 A1    11/2006   Austin et al.
2013/0337066 A1*   12/2013   Zhang ............... A61K 39/0011
                                                              424/489

FOREIGN PATENT DOCUMENTS

JP        07-083927 A       3/1995

OTHER PUBLICATIONS

Phyllis J. Fisher et al., 'Enhanced biological cathodoluminescence', Optics Communications, vol. 281, Issue 7, Apr. 1, 2008, pp. 1901-1908.

(Continued)

*Primary Examiner* — Melanie Y Brown
(74) *Attorney, Agent, or Firm* — Elizabeth Kim Patent Law Offices LLC (57) ABSTRACT

Multi-color CL images of nanoparticle samples may be generated, by irradiating with a scanning electron beam a nanoparticle sample that containing a plurality of spectrally distinct optical emitters configured to generate CL light at respective different color channels, then detecting the CL light from the nanoparticles to generate multi-color NP-CL images of the nanoparticle sample. In some embodiments, SE (secondary electron) images of the sample may be acquire, substantially simultaneously with the acquisition of the CL images, so as to generate correlative NP-CL and SE images of the nanoparticle sample. In some embodiments, (Continued)

the nanoparticles may be surface-functionalized so that the nanoparticles selectively bind only to particular structures of interest.

8 Claims, 5 Drawing Sheets

(51) Int. Cl.
    *H01J 37/244*     (2006.01)
    *G01N 33/543*     (2006.01)

(52) U.S. Cl.
    CPC ...... *H01J 37/244* (2013.01); *G01N 2223/403* (2013.01); *G01N 2223/418* (2013.01); *G01N 2223/612* (2013.01); *H01J 2237/225* (2013.01); *H01J 2237/2808* (2013.01)

(56) References Cited

OTHER PUBLICATIONS

Shuang Fang Lim et al., 'In Vivo and Scanning Electron Microscopy Imaging of Upconverting Nanophosphors in Caenorhabditis Elegans', Nano Lett., 2006, 6(2), pp. 169-174.

"International Search Report" for PCT/US2012/042332, 3 pages, Korean Intellectual Property Office, Daejeon Metropolitan City, Republic of Korea, Jan. 24, 2013.

* cited by examiner

MULTI-COLOR NANOSCALE IMAGING BASED ON NANOPARTICLE CATHODOLUMINESCENCE

CROSS-REFERENCE TO RELATED APPLICATIONS

This application is a 35 U.S.C. §371 National Phase Entry Application of International Application No. PCT/US12/42332 filed Jun. 13, 2012, which designates the U.S., and which claims the benefit of priority under 35 U.S.C. §119(e) of United States Provisional Patent Application No. 61/496,482 (the "'482 provisional application"), filed Jun. 13, 2011, and entitled "Multi-Color Electron Microscopy Based on Nanoparticle Cathodoluminescence." The content of each of these applications are incorporated herein by reference in their entireties.

STATEMENT REGARDING FEDERALLY SPONSORED RESEARCH

This invention was made with government support under contract number 60NANB10D002 awarded by NIST (National Institute Of Standards And Technology). The government has certain rights in the invention.

BACKGROUND

Electron microscopy, for example SEM (scanning electron microscopy), is a powerful imaging modality that provides structural information at high spatial resolutions, typically a few nm (nanometers), due to the short DeBroglie wavelength of electrons at keV energies.

The interaction of keV electrons with a solid can produce CL (cathodoluminescent) photons, a phenomenon widely used for spatially-resolved characterization of semiconductors and insulators. For a variety of applications, including without limitation bio-imaging, it is desirable to supplement SEM structural data with functional information obtained by optical microscopy.

For imaging biological samples, the potential of CL to provide molecular localization has been recognized for some time. However, efforts to obtain nanoscale CL image resolution have been hindered by low photon count rates and rapid signal degradation due to the destruction of biomolecules and organic fluorophores under electron beam irradiation.

BRIEF DESCRIPTION OF THE DRAWINGS

The drawings disclose illustrative embodiments. They do not set forth all embodiments. Other embodiments may be used in addition or instead.

DESCRIPTION

Illustrative embodiments are discussed in this disclosure. Other embodiments may be used in addition or instead.

It should be understood that the invention is not limited to the particular embodiments described, as such may vary. The terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

Figure 1:
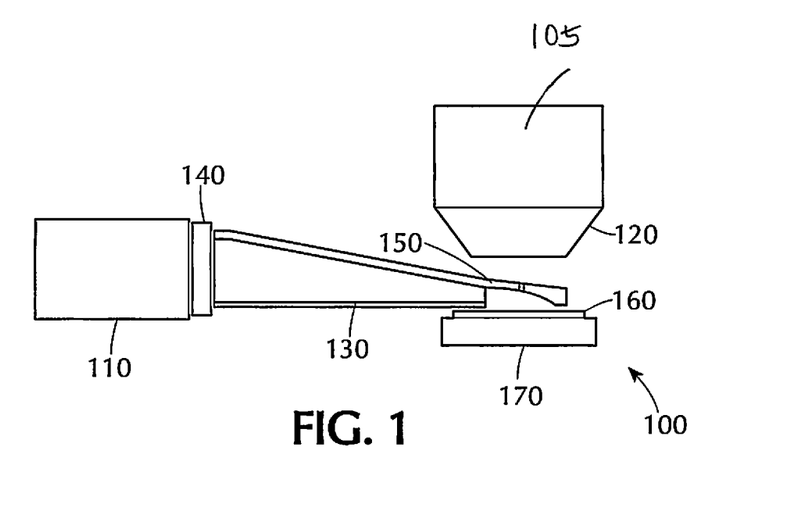
FIG. 1 is a schematic block diagram of a system for correlated CL and SE (secondary electron) imaging, in accordance with one embodiment of the present application.

In the present disclosure, methods and systems are described for generating multi-color optical CL images of nanoparticle samples that are produced using nanoparticles that have spectrally-distinct luminescent defects. In some embodiments, FIG. 1 is a schematic block diagram of a system 100 for correlative CL and SE imaging, in accordance with one embodiment of the present application. In overview, the system 100 includes an electron microscope 105 configured to generate an image of a nanoparticle sample that contains a plurality of nanoparticles, by irradiating the nanoparticle sample with electron beams. The nanoparticles include a plurality of spectrally distinct optical emitters which generate CL (cathodoluminescent) light at respective different color channels, in response to the electron beams from the electron microscope.

In the illustrated embodiment, the electron microscope is an SEM (scanning electron microscope), having an SEM pole piece 120. The SEM may be a field emission SEM. Other types of electron microscopes that may be used include, without limitation: an STM (scanning tunneling microscope); an STEM (scanning transmission electron microscope) and a TEM (transmission electron microscope).

The system 100 also includes a CL detection system configured to detect the CL light from the nanoparticles and to generate multi-color CL images of the nanoparticle sample. In the illustrated embodiment, the CL detection system is a spectrally selective, PMT (photomultiplier)—based CL detection system, configured to perform spectrally-selective imaging of nanoparticle cathodoluminescence. The PMT portion of the spectrally selective CL detection system is indicated in FIG. 1 by reference numeral 110.

In some embodiments, including the embodiment shown in FIG. 1, the electron microscope 105 and the CL detection system are integrated into a single instrument.

In the embodiment illustrated in FIG. 1, the SEM 105 is a field emission SEM (JEOL JSM-7001F) that is outfitted with a spectrally-selective, PMT-based CL detection system. In the illustrated embodiment, the NP (nanoparticle) samples are mounted on a silicon wafer 160 (placed on a sample holder 160), and excited by a scanning electron beam from the electron microscope 105. The resulting CL photons are collected by an elliptical mirror 150 and directed through a reflective light guide 130 onto the photomultiplier tube (PMT) 110. One or more wavelength-selective optical interference filters 140 are used to select CL light from only one of the NP species at a time. NP-CL spectra are used to select optical interference filters, with pass-bands indicated by colored rectangles, for multi-color CL imaging.

Figure 2:
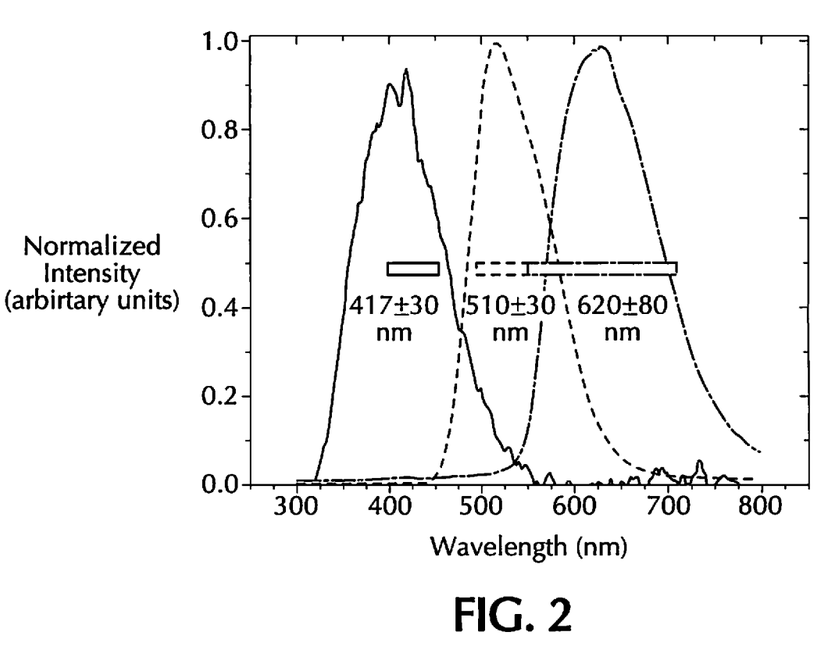
FIG. 2 illustrates CL spectra acquired with a scanning transmission electron microscope (STEM) for three species of semiconductor nanoparticles.

FIG. 2 is a plot of CL spectra acquired with a scanning transmission electron microscope (STEM) for three species of semiconductor nanoparticles. The spectrum that is plotted with a solid line was generated from nanodiamonds implanted with NV (nitrogen-vacancy) centers that produce red CL light, at a wavelength of about 620 nm. The spectrum plotted with a dashed line was generated from LuAG:Ce nanophosphors that produce green CL light, at a wavelength of about 510 nm. The spectrum plotted with a dash-dotted line was generated from nanodiamonds that contain band-A defects and generate blue CL light, at a wavelength of about 420 nm. Normalized NP-CL spectra were used to select optical interference filters, with pass-bands indicated by the solid, dashed, and dash-dotted rectangles in the figure, for multi-color CL imaging.

The above-described nanodiamonds containing NV centers have about 100 ppm nitrogen impurities, and were irradiated with He ions and annealed to promote NV formation. Dynamic light scattering (DLS) measurements of the NV nanodiamonds gave a mean particle size of 82±22 nm in an aqueous suspension. The above-described nanodiamonds containing high concentrations of 'band-A' defects were type 1a natural nanodiamonds, and had DLS-measured mean particle size of 48±14 nm. DLS measurements of the above-described LuAG:Ce nanophosphors gave a mean particle size of 37±13 nm.

Figure 3:
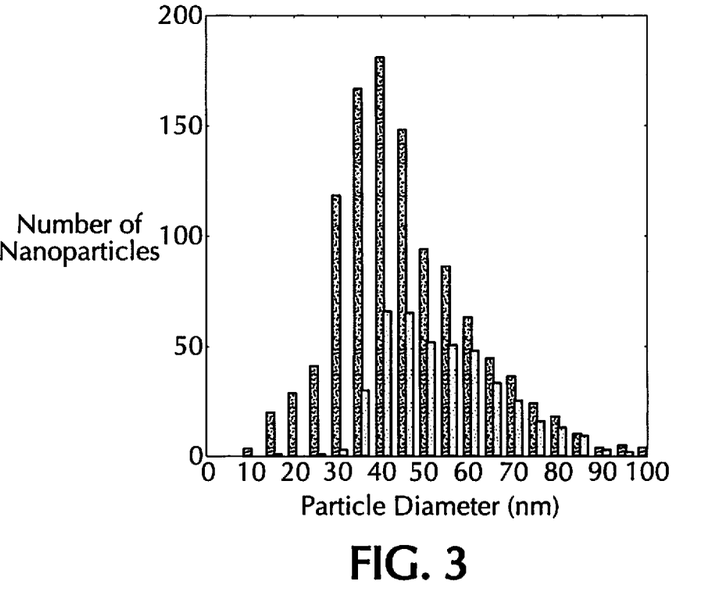
FIG. 3 shows the size and CL brightness distribution for nanoparticles used in one embodiment of the present disclosure.

FIG. 3 is a histogram illustrating the NP size and CL brightness distribution, i.e. stability of CL emission, for one of the above-described species of nanoparticles. In particular, the histogram in FIG. 3 shows the CL brightness distribution for LuAG:Ce NPs. The dense dark bars in FIG. 3 give size distribution for all NPs as measured by SE imaging. The lighter bars indicate NPs that produce detectable CL. For this NP type, the fraction of total NP population producing CL is ~0.42, with mean NP diameter of 54 nm.

Figure 4:
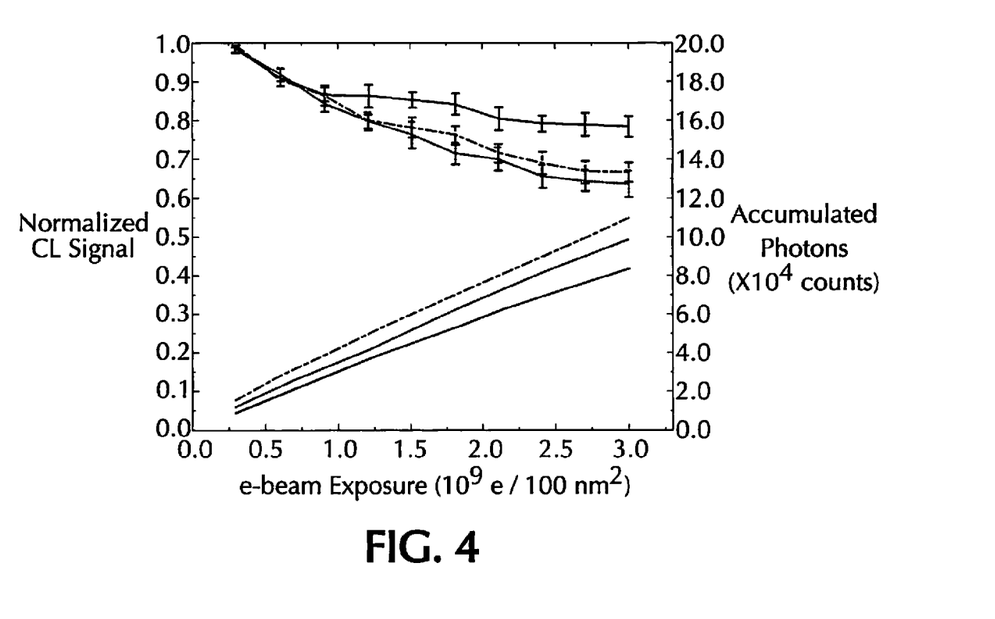
FIG. 4 illustrates the measured time-course of nanoparticle-cathodoluminescence signal.

FIG. 4 illustrates a measured time-course of a nanoparticle-cathodoluminescence signal. Measured time-course of NP-CL signal, showing good CL stability for large e-beam exposure. Solid lines and associated data points (left vertical axis) give average NP-CL signal from 10 CL-emitting NPs of each species over 10 full scans of the electron beam. The NP-CL signal for each NP was normalized to its value after the first scan before averaging over NPs. The selected NPs are representative of size distribution of CL-emitting particles for each species.

FIG. 4 shows that the NP-CL signal remains ~70% of initial value after a dose of ~109 electrons per NP, with decrease attributable in part to accumulation on NPs of hydrocarbon contaminants. In comparison, CL from organic fluorophores degrades to near-zero after dose of ~$10^7$ electrons per $(100 \text{ nm})^2$. The dashed lines and associated data points (right vertical axis) show total accumulated CL photon counts from a single NP of each species, selected from near the size distribution peak for that species. Selected NP FWHM diameters were found to be: $d_{Red}$=97 nm; $d_{Green}$=51 nm; $d_{Blue}$=75 nm.

In some embodiments, correlative SE and multi-color CL can be performed. In other words, SE and multi-color CL images can be acquired with nanoscale resolution, simultaneously and in the same instrument, for each of the three types of NPs. When compared with images taken with a confocal fluorescence microscope, the SE images have high spatial resolution (limited by e-beam diffraction), but are effectively monochromatic. The confocal images show distinct colors in fluorescence (essentially the same colors as for CL), but with photon-diffraction-limited resolution, which is insufficient to resolve individual NPs.

The NP-CL images, however, provide unique information, allowing both spectral discrimination between NP species, as well as image resolution of particles as small as ~30 nm. For many applications NP-CL can provide a considerable improvement over conventional EM techniques such as molecular labeling using gold nanoparticles, because the spectral distinguishability of the three NP markers allows spatial relationships between different molecular targets to be determined at nanoscale resolution.

Furthermore, the set of distinct NP-CL colors could be expanded by incorporating more than one type of defect in a NP, or by imaging at cryogenic temperatures to obtain narrower spectral lines. Importantly, the color separation of NP-CL is unambiguous and therefore constitutes a better labeling strategy.

Another major advantage of NP-CL imaging over previous approaches is that the CL signal can be ascertained at any resolution, whereas labeling with electron-scattering particles requires sufficient resolution to detect and/or discriminate between them. NP-CL is thus a multi-scale imaging technique.

In some embodiments, correlative NP-CL and SE imaging can be performed, i.e. correlated CL and SE images can be collected and acquired, as further described below. In this way, the advantages of both multicolor optical fluorescence and high-resolution electron microscopy can be combined, and NP-CL properties investigated.

For bioimaging applications, the robustness of NPs, i.e. their resistance of semiconductor NPs to damage under e-beam irradiation at keV energies is a key advantage compared to CL-emitting organic molecules. For each of the three types of semiconductor NPs, good luminescence stability was demonstrated by performing repeated CL imaging scans over a field of NPs deposited on a silicon wafer, as shown in FIGS. 3 and 4 described above. Even after 10 full scans, corresponding to a total dose of approximately ~$10^9$ electrons for a 50 nm particle, the CL signal for each type of NP showed only minor (~20-30%) decrease.

Many of the applications envisioned for correlated NP-CL and SE imaging may require targeted delivery of NPs to sites of interest, necessitating control over NP surface chemistry. In some embodiments, at least some of the nanoparticles are surface functionalized, so that each one of the surface-functionalized nanoparticles selectively binds only to a particular structure of interest.

In one embodiment, NP surface functionalization can be shown to be achieved while maintaining good CL properties, by using amine chemistry to bind antibodies tagged with a red fluorophore to blue-CL nanodiamonds. In one embodiment, a sample of these antibody-conjugated NPs were deposited onto a grid-etched silicon wafer, and imaged the sample in optical fluorescence followed by cathodoluminescence. These images show a high degree of spatial correlation, indicating that a large fraction (~0.71) of the NPs were successfully attached to fluorophore-tagged antibodies while still exhibiting good CL emission. Subsequent optical imaging showed almost no signal in the red channel due to degradation of the organic fluorophore under exposure to the electron beam, whereas the robust blue fluorescence was unchanged.

The above-described results demonstrate that correlative light and electron microscopy can be performed using multi-color cathodoluminescence from semiconductor nanoparticles. These nanoparticles may be controllably fabricated to contain spectrally distinct color centers and defects that are stable under prolonged electron-beam exposure, have excellent spectral separation, and be surface-functionalized to enable labeling of specific molecules and structures on a wide range of samples.

In some examples of operational regimes, the NP-CL imaging resolution may be set by particle size, which was 40-80 nm for the three types of NPs studied here. With optimized selection of small NPs having high defect concentration, NP-CL imaging resolution of about 30 nm may soon be available. Resolution of less than <10 nm may eventually be realized through ongoing improvements in fabrication of small NPs with high defect concentration. The speed and ease of multi-color NP-CL imaging may also be enhanced by optimization of CL optical collection efficiency and parallel imaging of different CL colors, e.g., with multiple CL detection paths or use of a broadband spectrograph.

Applications of the above-described correlated NP-CL and SE imaging may include nanoscale functional imaging in biological samples, e.g., in serial-SEM connectomics, where multi-color NP-CL may allow targeted identification of molecular markers such as neurotransmitter enzymes, postsynaptic receptor types, peptides, and calcium binding proteins that differentiate classes of neurons and synapses, and be correlated with nanoscale SE structural images of thin-slice (~30 nm) neural tissue.

Functionalized cathodoluminescent nanoparticles may open up powerful new avenues for correlative optical and electron microscopy in the physical and life sciences, allowing both molecular localization and structural imaging to be achieved at nanometer resolution. In some embodiments, such correlative optical and electron microscopy may be performed simultaneously and using a single integrated instrument.

Figure 5:
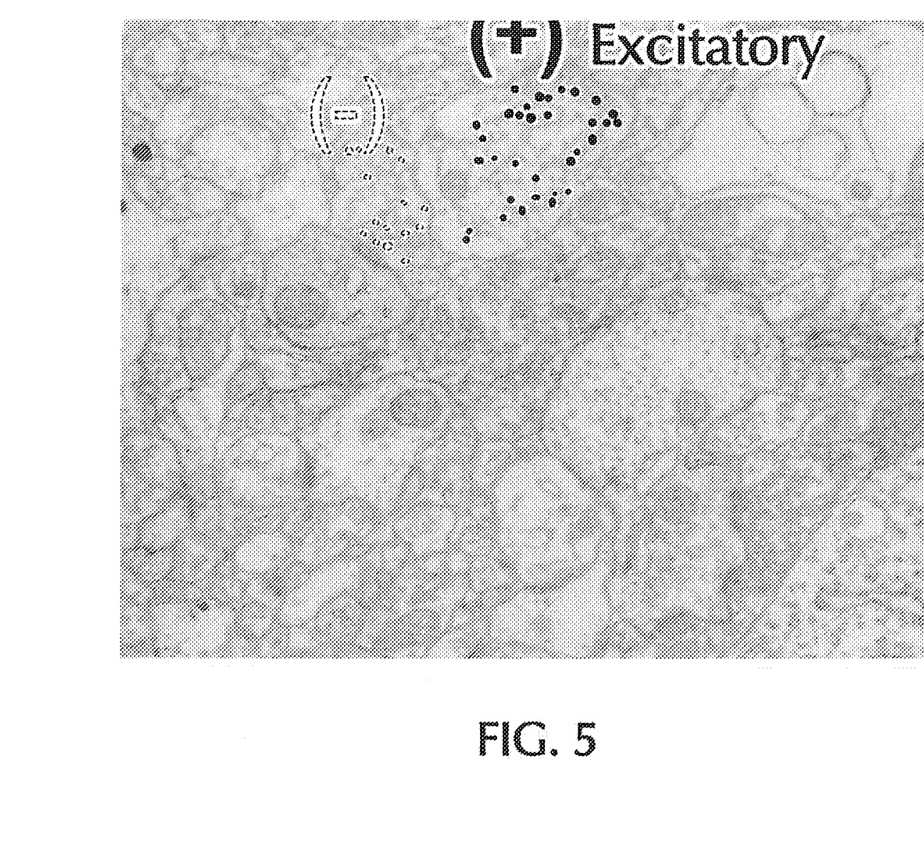
FIG. 5 illustrates a possible application of multicolor nanoscale imaging to connectomics.

FIG. 5 illustrates a possible application of multicolor nanoscale imaging to connectomics. Connectomics is an emerging field defined by high-throughput generation of data about neural connectivity and the subsequent mining of that data for knowledge about the brain. To resolve individual synapses requires electron microscopy and ultra-thin serial sectioning. The use of nanodiamond CL in connectomics can be useful in reducing segmentation errors: process-specific CL emitters of different colors, or combinations of colors, can label corresponding regions in each slice, facilitating automated matching/error checking.

As seen in FIG. 5, by using NPs that are functionalized to bind to particular structures of interest, for example, synaptic vesicles, distinctions can be made which cannot be done with SEM images alone. As seen in FIG. 5, correlative multi-color CL-SE imaging with functionalized nanoparticles allows for distinguishing between excitatory synapses (shown in FIG. 5 as black filled dots) and inhibitory synapses (shown in FIG. 5 as unfilled dots).

To summarize, the methods described in this application include irradiating with a scanning electron beam a nanoparticle sample containing a plurality of nanoparticles, so as to cause emission of CL photons from the nanoparticle sample, the nanoparticles including a plurality of spectrally distinct optical emitters configured to generate CL light at respective different color channels. The CL light is then detected from the nanoparticles to generate multi-color NP-CL images of the nanoparticle sample.

In some embodiments, correlative NP-CL and SE images of the nanoparticle sample may be generated by acquiring SE images of the sample, substantially simultaneously with the acquisition of the CL images. In some embodiments, the nanoparticles may be surface-functionalized, so that the nanoparticles can selectively bind only to a particular structure of interest. For example, the surface of each nanoparticle may be coated with a predetermined substance so that the nanoparticle becomes conjugated with a particular antibody.

Nothing that has been stated or illustrated is intended to cause a dedication of any component, step, feature, object, benefit, advantage, or equivalent to the public. While the specification describes particular embodiments of the present disclosure, those of ordinary skill can devise variations of the present disclosure without departing from the inventive concepts disclosed in the disclosure.

While certain embodiments have been described, it is to be understood that the concepts implicit in these embodiments may be used in other embodiments as well. In the present disclosure, reference to an element in the singular is not intended to mean "one and only one" unless specifically so stated, but rather "one or more." All structural and functional equivalents to the elements of the various embodiments described throughout this disclosure, known or later come to be known to those of ordinary skill in the art, are expressly incorporated herein by reference.

What is claimed is:

1. A system comprising:
    an electron microscope configured to generate an image of a nanoparticle sample containing a plurality of nanoparticles, by irradiating the nanoparticle sample with electron beams;
    wherein the nanoparticles comprise a plurality of spectrally distinct optical emitters configured to generate CL (cathodoluminescent) light at respective different color channels in response to the electron beams from the electron microscope; and
    a CL detecting imaging system configured to detect the CL light from the nanoparticles and to generate multi-color CL images of the nanoparticle sample;
    wherein the nanoparticles comprise nanodiamonds that contain NV (nitrogen-vacancy) color centers, and that are configured to produce red cathodoluminescent light at a wavelength of about 620 nm.

2. The system of claim 1, wherein the nanoparticles further comprise LuAG:Ce (Cerium-doped Lutetium-Aluminum) nanophosphors that are configured to produce green cathodoluminescent light at a wavelength of about 510 nm.

3. The system of claim 1, wherein the Nanoparticles further comprise nanodiamonds that include band-A defects and that are configured to produce blue cathodoluminescent light at a wavelength of about 420 nm.

4. The system of claim 1, wherein the electron microscope and the CL imaging system are integrated into a single instrument.

5. The system of claim 1, wherein the electron microscope comprises one of a SEM (scanning electron microscope); an STM (scanning tunneling microscope); an STEM (scanning transmission electron microscope) and a TEM (transmission electron microscope).

6. The system of claim 1, wherein at least some of the nanoparticles are surface functionalized, so that each one of the surface-functionalized nanoparticles selectively binds only to a particular structure of interest.

7. The system of claim 6, wherein the surface-functionalized nanoparticles comprise antibody-conjugated nanoparticles.

8. The system of claim 6, wherein the particular structures of interest comprise synaptic vesicles.

\* \* \* \* \*

UNITED STATES PATENT AND TRADEMARK OFFICE
CERTIFICATE OF CORRECTION

| | | |
|---|---|---|
| PATENT NO. | : 9,541,512 B2 | Page 1 of 1 |
| APPLICATION NO. | : 14/125934 | |
| DATED | : January 10, 2017 | |
| INVENTOR(S) | : Walsworth et al. | |

It is certified that error appears in the above-identified patent and that said Letters Patent is hereby corrected as shown below:

In the Specification

Delete the paragraph beginning at Column 1, Line number 20:
"STATEMENT REGARDING FEDERALLY SPONSORED RESEARCH
This invention was made with government support under contract number 60NANB10D002 awarded by NIST (National Institute of Standards And Technology). The government has certain rights in the invention."

Signed and Sealed this
Thirtieth Day of September, 2025

John A. Squires
*Director of the United States Patent and Trademark Office*